United States Patent
Vernickel et al.

(10) Patent No.: US 10,441,218 B2
(45) Date of Patent: Oct. 15, 2019

(54) OSCILLATION APPLICATOR FOR MR RHEOLOGY

(71) Applicant: KONINKLIJKE PHILIPS N.V., Eindhoven (NL)

(72) Inventors: Peter Vernickel, Hamburg (DE); Christoph Leussler, Hamburg (DE); Daniel Wirtz, Hamburg (DE); Peter Mazurkewitz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/406,388

(22) PCT Filed: May 30, 2013

(86) PCT No.: PCT/IB2013/054457
§ 371 (c)(1),
(2) Date: Dec. 8, 2014

(87) PCT Pub. No.: WO2013/186658
PCT Pub. Date: Dec. 19, 2013

(65) Prior Publication Data
US 2015/0148663 A1   May 28, 2015

Related U.S. Application Data

(60) Provisional application No. 61/658,480, filed on Jun. 12, 2012.

(30) Foreign Application Priority Data

Jun. 12, 2012  (EP) .................................... 12171571

(51) Int. Cl.
*A61B 5/00* (2006.01)
*G01R 33/563* (2006.01)
(Continued)

(52) U.S. Cl.
CPC .......... *A61B 5/6831* (2013.01); *A61B 5/6843* (2013.01); *G01R 33/3415* (2013.01);
(Continued)

(58) Field of Classification Search
CPC .... A61B 5/6831; A61B 5/6843; G01R 33/28; G01R 33/30; G01R 33/3415; G01R 33/50; G01R 33/5608; G01R 33/56358
See application file for complete search history.

(56) References Cited

U.S. PATENT DOCUMENTS 3,520,294 A * 7/1970 Fuzzell ................ A61B 5/1135
338/47
4,907,595 A * 3/1990 Strauss ..................... A61B 8/02
600/452
(Continued)

OTHER PUBLICATIONS

Motosugi, Utaroh. et al "Effects of Gadoxetic Acid on Liver Elasticity Measurement by using Magnetic Resonance Elastography", Magnetic Resonance Imaging, vol. 30, No. 1, Aug. 2011, pp. 128-132.
(Continued)

*Primary Examiner* — Katherine L Fernandez

(57) ABSTRACT

The invention relates to the field of magnetic resonance (MR) imaging. It concerns an oscillation applicator for MR rheology. It is an object of the invention to provide an oscillation applicator without restrictions regarding the usability for certain body regions. According to the invention, the oscillation applicator comprises at least one transducer which generates a reciprocating motion at a given frequency and a belt (19) mechanically coupled to the transducer, which belt (19) is designed to be wrapped around a patient's body (10). Moreover, the invention relates to a MR device (1) and to a method of MR imaging.

5 Claims, 3 Drawing Sheets

(51) Int. Cl.
*G01R 33/3415* (2006.01)
*G01R 33/50* (2006.01)
*G01R 33/56* (2006.01)

(52) U.S. Cl.
CPC ......... *G01R 33/50* (2013.01); *G01R 33/5608* (2013.01); *G01R 33/56358* (2013.01)

(56) References Cited

U.S. PATENT DOCUMENTS

| | | | |
|---|---|---|---|
| 5,913,834 A | 6/1999 | Francais | |
| 5,952,828 A * | 9/1999 | Rossman | A61B 5/055 |
| | | | 324/318 |
| 6,184,684 B1 | 2/2001 | Dumoulin et al. | |
| 6,506,175 B1 * | 1/2003 | Goldstein | A61F 13/06 |
| | | | 602/60 |
| 6,833,703 B2 | 12/2004 | Sinkus | |
| 6,879,155 B2 | 4/2005 | Ehman | |
| 9,492,105 B1 * | 11/2016 | Kayyali | A61B 5/08 |
| 2004/0226972 A1 * | 11/2004 | Cook | A45F 5/021 |
| | | | 224/195 |
| 2005/0165445 A1 * | 7/2005 | Buckman | A61F 13/00 |
| | | | 606/213 |
| 2006/0253020 A1 | 11/2006 | Ehman | |
| 2006/0253030 A1 | 11/2006 | Altmann | |
| 2008/0221525 A1 * | 9/2008 | Manzano-Rivera | |
| | | | A61M 25/02 |
| | | | 604/179 |
| 2008/0262347 A1 * | 10/2008 | Batchelder | A61B 5/6828 |
| | | | 600/437 |
| 2009/0140739 A1 | 6/2009 | Bennett | |
| 2009/0209847 A1 | 8/2009 | Li | |
| 2009/0295387 A1 * | 12/2009 | Ehman | A61B 5/416 |
| | | | 324/309 |
| 2009/0299168 A1 | 12/2009 | Ehman et al. | |
| 2010/0049029 A1 * | 2/2010 | Li | G01R 33/28 |
| | | | 600/410 |
| 2010/0152564 A1 * | 6/2010 | Nguyen | A61B 5/0444 |
| | | | 600/390 |
| 2012/0065494 A1 * | 3/2012 | Gertner | A61B 5/055 |
| | | | 600/411 |
| 2013/0211772 A1 * | 8/2013 | Ross, Jr. | A61B 5/6831 |
| | | | 702/141 |
| 2013/0239690 A1 | 9/2013 | Tadano et al. | |

OTHER PUBLICATIONS

Tse, Z.T.H. et al "Magnetic Resonance Elastogrpahy Hardware Design: A Survey", Proceedings of the Institution of Mechanical Enginners, Journal of Engineering in Medicine, vol. 223, No. 4, May 2009.

Oida et al "Magnetic Resonance Elastography: In Vivo Measurements of Elasticity for Human Tissue" Kyoto University (2004).

Weaver et al "MR Elastographic Methods for the Evaluation of Plantar Fat Pads: Preliminary Comparsion of the Shear Modulus . . . " SPIE, vol. 6143, Mar. 13, 2006.

* cited by examiner

OSCILLATION APPLICATOR FOR MR RHEOLOGY

CROSS-REFERENCE TO PRIOR APPLICATIONS

This application is the U.S. National Phase application under 35 U.S.C. § 371 of International Application No. PCT/IB2013/054457, filed on May 30, 2013, which claims the benefit of U.S. Provisional Patent Application No. 61/658,480, filed on Jun. 12, 2012 and European Patent Application No. 12171571.8, filed on Jun. 12, 2012. These applications are hereby incorporated by reference herein.

TECHNICAL FIELD

The invention relates to the field of magnetic resonance (MR) imaging. It concerns an oscillation applicator for MR rheology. Moreover, the invention relates to a MR device and to a MR imaging method.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field of the RF pulse extends perpendicular to the z-axis, so that the magnetization performs a precession about the z-axis. This motion of the magnetization describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°). The RF pulse is radiated toward the body of the patient via a RF coil arrangement of the MR device. The RF coil arrangement typically surrounds the examination volume in which the body of the patient is placed.

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF antennas or coils which are arranged and oriented within the examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving RF antennas or coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation or by other per se known reconstruction techniques.

MR rheology has become known recently as a promising technique for gathering diagnostically useful additional information on tissue properties that are not accessible via conventional MR imaging alone. MR rheology utilizes the fact that the MR signal phase in a MR image of the examined object changes under the influence of mechanical oscillations acting on the examined object. The extent of this change is dependent on the local deflection of the tissue caused by the mechanical oscillations. Information regarding mechanical parameters of the tissue, for example, concerning the viscosity or elasticity, can thus be derived from MR phase images acquired from the examined object while mechanical oscillations are acting on the object. A MR phase image means in this context a MR image reproducing the spatial distribution of the phase of the nuclear magnetization.

The mentioned mechanical parameters accessible via MR rheology, like tissue viscosity or elasticity, can otherwise only be determined invasively by means of biopsy and/or histology. On the other hand, it is known that these parameters directly link to, for example, cirrhotic or cancerous changes in liver, breast or brain tissue. It has been demonstrated that MR rheology is especially useful for diagnosis of liver cirrhosis and to determine the stage of liver cirrhosis. Further, MR rheology has been proven to be useful for the diagnosis of breast cancer. Initial applications for the examination of degenerative brain diseases by means of MR rheology have been reported.

In a typical MR rheology setup provision is made for at least one transducer which generates a reciprocating motion at a given frequency. The transducer excites mechanical oscillations in the tissue of the patient's body. Moreover, provision is made for an appropriate arrangement of RF coils for generating MR images of the anatomical background. Basically, the transducer excites a mechanical wave propagating inside the body tissue, wherein the propagation direction is perpendicular to the body surface to which the transducer is attached. An important pre-requisite is good mechanical coupling of the transducer to the patient's body.

An oscillation applicator useable for MR rheology is for example known from U.S. Pat. No. 6,833,703 B2. This known applicator is designed as a mammography accessory for MR rheology which is capable of generating longitudinal oscillations extending in the longitudinal direction in the mammae of a patient to be examined. The known applicator is integrated into the patient table of the MR device and provides good coupling of the transducer to the body.

One drawback of known designs of oscillation applicators for MR rheology is that positioning of the applicator on the patient's body is not possible for all required imaging positions. A further issue is that transducers based on electro-magnetic drives (such like electric motors or linear electro-magnetic oscillators) interact with the main magnetic field $B_0$. Consequently, such transducers can be positioned within the examination volume of the MR device only in such a manner that the magnetic fields generated by the electro-magnetic drives is oriented perpendicular to the field lines of the main magnetic field $B_0$. This restricts the placement of the oscillation applicator and, consequently, the application of MR rheology for certain body regions.

The paper 'Effects of gadoxetic acid on liver elasticity measurement by usiing magnetic resonance elastography' by U. Motosugi et al. in Magn. Res. Im. 30(2011)128-132 mentions the use of a passive driver attached to an elastic belt to deliver vibrations to the patient's chest and liver.

From the foregoing it is readily appreciated that there is a need for an improved oscillation applicator for MR rheology.

SUMMARY OF THE INVENTION

In accordance with the invention, an oscillation applicator for MR rheology is disclosed. The oscillation applicator of the invention comprises:
- at least one transducer which generates a reciprocating motion at a given frequency;
- a belt mechanically coupled to the transducer, which is designed to be wrapped around a patient's body and each of a plurality of transducers is coupled to the belt) at a different position along its longitudinal extension.

According to the invention that the belt is mechanically coupled to the transducer such that the transducer is held in place on the patient's body by means of the belt, while the belt is wrapped around the patient's body. The belt itself provides the mechanical coupling between the transducer and the patient's body. The reciprocating motion generated by the transducer is acting on the patient's body via the belt. Preferably, the belt is not stretchable in order to efficiently couple the mechanical oscillations into the body. A mechanical support or certain mass or weight of the oscillation applicator is not required according to the invention. The oscillation applicator of the invention can be used for MR rheology examination of virtually every portion of the patient's body. Moreover, the workflow of a MR rheology examination can be improved by using the oscillation applicator of the invention, since the invention enables to fix the oscillation applicator relatively to the patient during preparation, i.e. before the patient is placed within the examination volume of the MR device for MR signal acquisition.

According to the invention, the at least one transducer generates a reciprocating motion at a given frequency. This includes the possibility that a reciprocating motion having a spectrum comprising different frequency components is generated by the transducer.

According to a preferred embodiment of the invention, the width of the belt varies along its length. In this way, the belt can be shaped in a targeted manner in order to control the pressure exerted on the body surface. This can be used to achieve a required oscillation of tissue or to protect sensible body portions.

In the known design (U.S. Pat. No. 6,833,703 B2, see above) a reciprocating motion perpendicular to the body surface is generated. Oscillation applicators generating a motion parallel to the body surface require a certain amount of adhesion, which is not always given. The belt as proposed according to the invention can be used to transform a parallel oscillation of the transducer to a motion perpendicular to at least a part of the surface of the patient's body. This allows for more degrees of freedom in designing the oscillation applicator. The size of the applicator is crucial for workflow and patient comfort. When the ends of the belt are attached to the oscillating parts of the transducer (i.e. periodically changing their distance along the body surface), the belt turns the oscillation into an inward/outward directed motion since the change of the circumference of the belt forming a closed loop results in a corresponding change of the radius.

According to a possible variant, the reciprocating motion generated by the transducer runs parallel to the longitudinal axis of the belt and tangential to the surface of the body. In an alternative variant, the reciprocating motion generated by the transducer runs orthogonal to the longitudinal axis of the belt and perpendicular to the surface of the body. In this way it is possible to produce predominantly either longitudinal or transversal mechanical waves propagating within the body tissue. Thereby it becomes possible to investigate mechanical parameters having tensor properties.

According to another preferred embodiment of the invention, the at least one transducer of the oscillation applicator is arranged in an oscillator housing which is attached to the belt. The housing encloses and protects the components of the transducer. Moreover, the housing can be used as a part of the mechanical coupling of the transducer to the belt.

According to the invention, a plurality of transducers is coupled to the belt at different positions along its longitudinal extension. The different transducers can be individually driven to achieve complex patterns of the mechanical waves propagating within the body tissue. To this end, the reciprocating motion generated by each transducer should have an individually controllable amplitude, frequency and phase. The amplitude can be locally optimized by constructive/destructive superposition/interference of the individual waves. An iterative software algorithm, which uses preset values as start values is run during preparation time. During the MR sequence, the amplitude, frequency and phase can change due to motion of the human body or other reasons, which might support the reconstruction of clinical relevant parameters.

Moreover, the mechanical oscillations can be applied at different positions of the body surface without repositioning of the applicator.

According to yet another preferred embodiment of the invention, at least one cushion is attached to the belt, which cushion is to be placed between the belt and the patient's body. The cushion serves for controlling the pressure exerted on the body surface at the position of the cushion. More flexible cushions can be used for preventing mechanical coupling at certain body positions. A less flexible cushion can be used to focus the application of the mechanical oscillations at a certain body position. In this way, the place of the strongest mechanical coupling between transducer and body can be controlled. There is no need to place the oscillatior itself where the strongest force/motion is required. Instead the cuhion might be used to focus the force. The belt transmits the force/motion from the transducer to the focussing cushion.

According to still another preferred embodiment of the invention, the transducer comprises a drive and a transmission element, via which the drive is coupled to the belt. The transmission element may be a Bowden cable or a flexible shaft. The transmission element transmits the driving force of the drive to the belt, wherein the length of the transmission line is limited only by friction and losses of the transmission element. This embodiment of the invention has the advantage that the drive, which may be an electric motor or a linear electro-magnetic drive (comprising, for example, a coil and a permanent magnet, like in a conventional loudspeaker design) can be located outside the examination volume of the used MR device. In this way, undesirable interactions of the magnetic fields of the drive with the main magnetic field $B_0$ of the MR device are avoided. The drive may be positioned at a distance of one meter or more from the iso-centre of the main magnet of the MR device.

The invention does not only relate to an oscillation applicator, but also to a MR imaging device. The device comprises:
- at least one main magnet coil for generating a uniform, steady main magnetic field within an examination volume,
- a number of gradient coils for generating switched magnetic field gradients in different spatial directions within the examination volume,
- at least one RF coil for generating RF pulses at a MR resonance frequency within the examination volume and/or for receiving MR signals from a body of a patient positioned in the examination volume,
- a control unit for controlling the temporal succession of RF pulses and switched magnetic field gradients,
- a reconstruction unit for reconstructing a MR image from the received MR signals;
- an oscillation applicator of the type specified above.

The oscillation applicator according to the invention can advantageously be used in combination with most MR imaging devices presently being used in clinical practice, wherein the belt of the oscillation applicator is wrapped around the portion of the patient to be examined.

Moreover, the invention relates to Method of MR imaging of at least a portion of a body placed in a magnetic field within the examination volume of a MR device. The method comprises the following steps:
- subjecting the portion of the body to an oscillating mechanical excitation by means of an oscillation applicator of the type specified herein above, wherein the belt of the oscillation applicator is wrapped around the portion of the body;
- subjecting the portion of the body to an imaging sequence comprising one or more RF pulses and switched magnetic field gradients, whereby MR signals are acquired from the portion of the body;
- deriving spatially resolved parameters reflecting the elasticity and/or the viscosity of the tissue of the body from the acquired MR signals.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
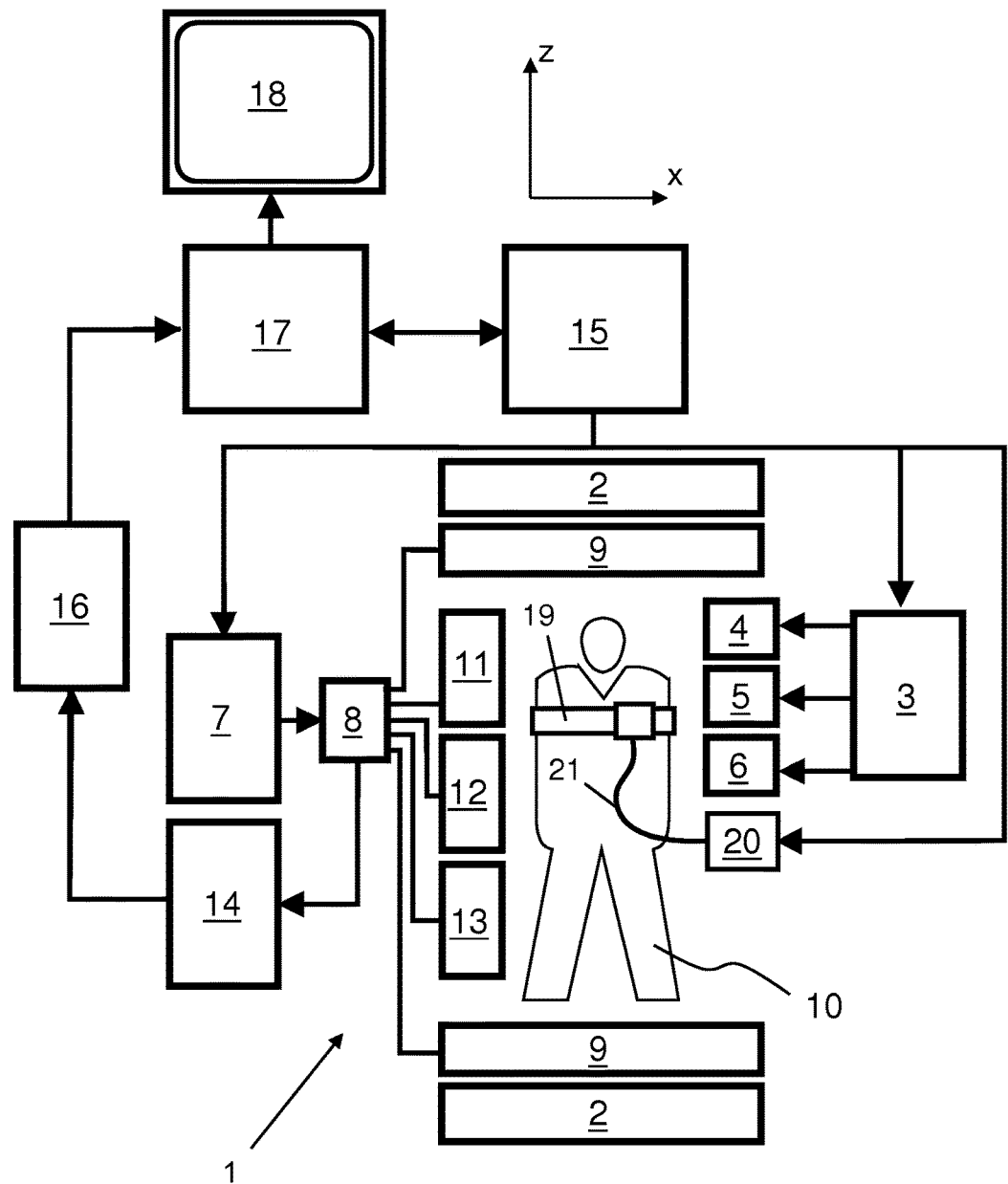
FIG. 1 schematically shows a MR device according to the invention.

With reference to FIG. 1, a MR imaging device 1 is shown. The device comprises superconducting or resistive main magnet coils 2 such that a substantially uniform, temporally constant main magnetic field is created along a z-axis through an examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a whole-body volume RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the whole-body volume RF coil 9.

For generation of MR images of limited regions of the body 10, a set of local array RF coils 11, 12, 13 are placed contiguous to the region selected for imaging. The array coils 11, 12, 13 can be used for parallel imaging to receive MR signals induced by body-coil RF transmissions.

The resultant MR signals are picked up by the whole body volume RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a appropriate reconstruction algorithms. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

According to the invention, the MR device 1 further comprises an oscillation applicator for MR rheology. In a possible embodiment of the invention, the operation of the oscillation applicator may be based on an electro-mechanical converter, which transforms electrical signals to mechanical oscillations, e.g. by interacting with the main magnetic field $B_0$.

The oscillation applicator comprises a belt 19 which is wrapped around the patient's body 10. A transducer generating a reciprocating motion at a given frequency is part of the oscillation applicator. The transducer comprises a drive 20 and a transmission element 21, via which the drive 20 is coupled to the belt 19. The drive 20, which is controlled by the host computer 15 of the MR device 1, is located outside the examination volume of the MR device 1 such that the magnetic fields generated by the drive 20 do not interfere with the main magnetic field generated by the main magnet coils 2.

By means of the oscillation applicator the portion of the body 10 around which the belt 19 is wrapped is subjected to an oscillating mechanical excitation during MR signal acquisition. Spatially resolved parameters reflecting the elasticity and/or the viscosity of the tissue of the body 10 are derived from the acquired MR signals by means of the reconstruction processor 17.

Figure 2:
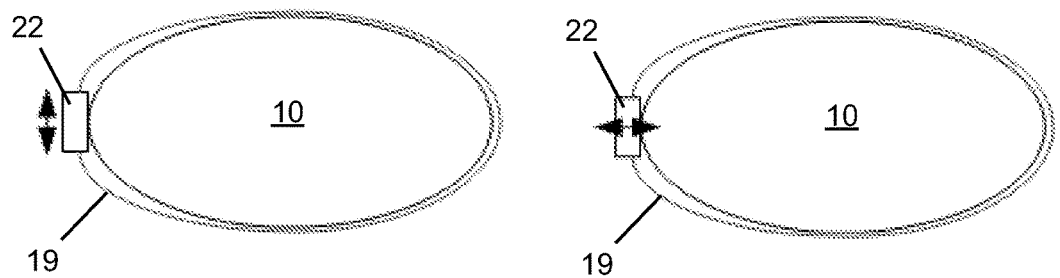
FIG. 2 illustrates the excitation of oscillations by means of the oscillation applicator according to the invention.

In FIG. 2, the excitation of oscillations by means of the oscillation applicator according to the invention is illustrated. In the depicted embodiment, the transducer of the oscillation applicator is arranged in an oscillator housing 22 which is attached to the belt 19. FIG. 2 shows a cross section of the portion of the patient's body 10 around which the belt 19 is wrapped. In the left image in FIG. 2, the reciprocating motion (indicated by the arrow) generated by the transducer runs parallel to the longitudinal axis of the belt 19 and tangential to the surface of the body 10. In the embodiment shown in the right image in FIG. 2, the reciprocating motion generated by the transducer runs orthogonal to the longitudinal axis of the belt 19 and perpendicular to the surface of the body 10.

Figure 3:
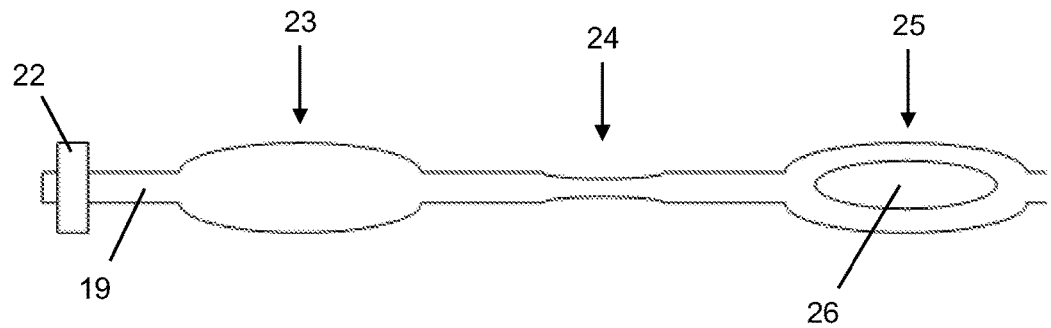
FIG. 3 shows an oscillation applicator according to the invention with varying belt width.

FIG. 3 illustrates how the force exerted on the body surface along the belt 19 can be controlled in a targeted manner. In the depicted embodiment, the belt 19 has a broader portion 23. The effect of the broader portion 23 is that the pressure exerted on the patient's body surface is decreased at the respective position. In a portion 24 of reduced width, in contrast, an increased pressure is exerted on the patient's body surface. The shaping of the belt will depend, in practice, on the respective rheology application and the patient's anatomy. An individually shaped belt with varying width along its length can be used to achieve a given oscillation pattern within the patient's body tissue or to protect sensible body regions. In a portion 25 of the belt 19 provision is made for a gap 26. The gap 26 can be used to enable access to the patient's body for intervention.

Figure 4:
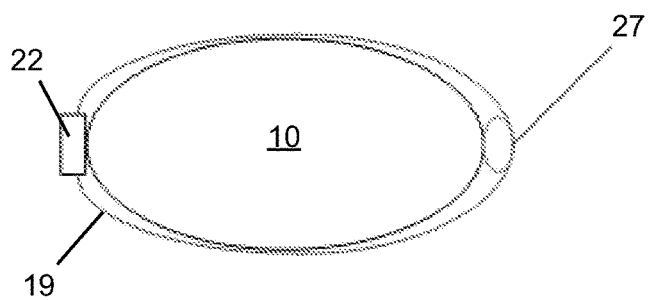
FIG. 4 shows an oscillation applicator according to the invention with integrated cushion.

FIG. 4 shows an embodiment of the invention, in which provision is made for a cushion 27. The cushion 27 is used for controlling the pressure exerted by the oscillation applicator on the patient's body 10. A highly flexible cushion may be coupled to the belt 19 for preventing mechanical coupling at the position at which the cushion 27 is in contact with the surface of the body 10. A less flexible cushion may be used to focus the pressure at the respective body position.

Figure 5:
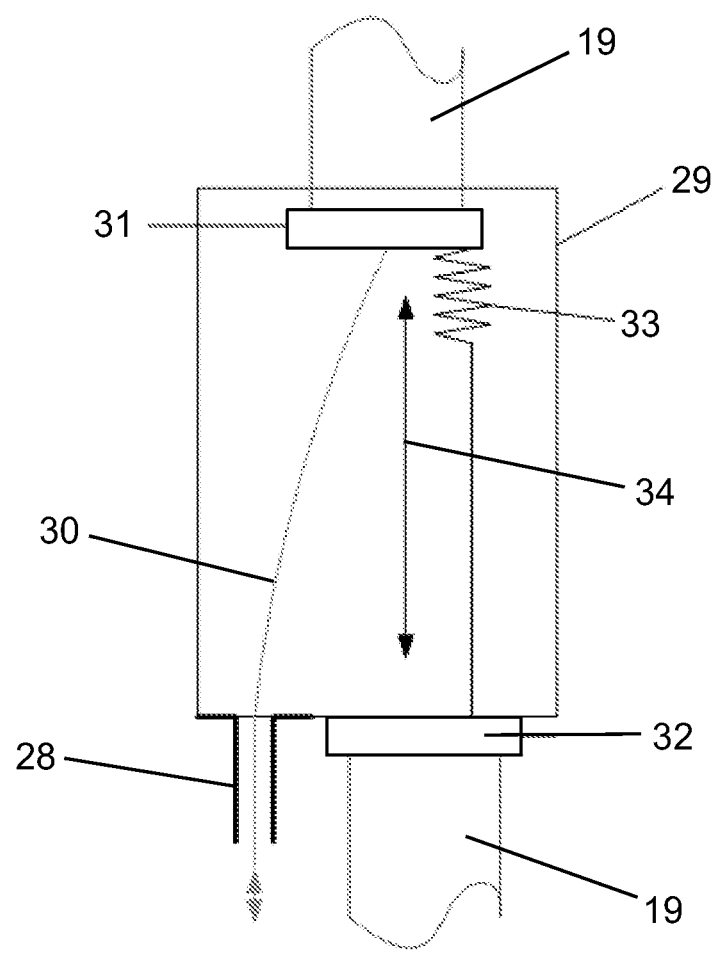
FIG. 5 shows an oscillation applicator according to the invention with a Bowden cable as transmission element.

FIG. 5 shows the design of an oscillation applicator which works well in combination with the belt design of the invention. A Bowden cable is used as a transmission element 21 (see FIG. 1). A sheath 28 of the Bowden cable is firmly connected to a rigid housing 29. A filament 30 of the Bowden cable is attached to an end 31 of the belt 19. The end 31 of the belt 19 is moveable relative to the housing 29. The other end 32 of the belt 19 is firmly attached to the housing 29. A reciprocating oscillating linear motion in the direction indicated by arrow 34 along the extension of the Bowden cable is generated by means of the drive 20 (see FIG. 1). This motion is transmitted via the filament 30 to the end 31 of the belt 19. A corresponding force is exerted on the patient's body 10 around which the belt 19 is wrapped. A restoring force is generated by the compressible body tissue such that, finally, the desired oscillation is excited within the patient's body 10. Optionally, a spring 33 may be provided between the end 31 of the belt 19 and the housing 29 in order to provide a bias for the oscillating force or to support the restoring force of the body tissue.

In an alternative embodiment (not depicted) provision may be made for differently arranged springs and levers within the housing 29 in order to generate the desired reciprocating motion at a given amplitude in a given direction.

In a further embodiment (not depicted) the transmission element 21 may be an elastic shaft which transmits a rotating motion from the drive 20 to the belt 19. An eccentric may be integrated into the housing 29 in order to produce the required oscillation.

The invention claimed is:

1. A method of magnetic resonance (MR) imaging of at least a portion of a body of a patient placed in a magnetic field within the examination volume of a MR device, the method comprising:
    subjecting the at least a portion of the body to an oscillating mechanical excitation using transducers configured to oscillate at a given frequency, wherein a belt of varying width is configured to convey oscillating motion of the transducers to the body, and wherein the subjecting the at least a portion of the body to the oscillating mechanical excitation is controlled by placing a portion of reduced width of the belt where it is desired to apply increased pressure;
    subjecting the at least a portion of the body to an imaging sequence comprising one or more radiofrequency (RF) pulses and switched magnetic field gradients, whereby MR signals are acquired from the at least a portion of the body; and
    deriving spatially resolved parameters reflecting the elasticity and/or the viscosity of a tissue of the body from the acquired MR signals.

2. The method of MR imaging according to claim 1, wherein at least one transducer of the transducers is arranged in an oscillator housing which is attached to the belt, and a spring is attached between an end of the belt and the oscillator housing.

3. The method of MR imaging according to claim 1, wherein the transducers are supported on an outside of the belt wrapped around the at least a portion of the body.

4. The method of MR imaging according to claim 1, further comprising accessing the patient for intervention through a gap portion of the belt.

5. The method of MR imaging according to claim 1, wherein the subjecting the at least a portion of the body to the oscillating mechanical excitation is further controlled by placing a broader portion of the belt in comparison to the portion of reduced width where it is desired to apply reduced pressure.

* * * * *